(12) United States Patent
He et al.

(10) Patent No.: US 7,132,282 B2
(45) Date of Patent: Nov. 7, 2006

(54) GENETIC MODIFICATION OF C57 MICE

(75) Inventors: Wei He, South Setauket, NY (US); Wei Weng, Patchogue, NY (US)

(73) Assignee: Ingenious Targeting Inc., Stony Brook, NY (US)

( * ) Notice: Subject to any disclaimer, the term of this patent is extended or adjusted under 35 U.S.C. 154(b) by 0 days.

(21) Appl. No.: 10/768,350

(22) Filed: Jan. 30, 2004

(65) Prior Publication Data

US 2005/0172349 A1    Aug. 4, 2005

(51) Int. Cl.
| | |
|---|---|
| *C12N 5/00* | (2006.01) |
| *C12N 5/02* | (2006.01) |
| *C12N 5/06* | (2006.01) |
| *C12N 5/10* | (2006.01) |
| *C12N 15/00* | (2006.01) |

(52) U.S. Cl. .................... 435/354; 435/325; 800/21; 800/25

(58) Field of Classification Search .................... 800/3, 800/8, 13, 18
See application file for complete search history.

(56) References Cited

U.S. PATENT DOCUMENTS

| | | |
|---|---|---|
| 2003/0037354 A1 | 2/2003 | Ornitz et al. |
| 2003/0154499 A1 | 8/2003 | Wasel-Nielsen et al. |
| 2003/0167015 A1 | 9/2003 | Roden et al. ............. 600/518 |

OTHER PUBLICATIONS

Kroll and Amaya, 1996, Development, 122:3173-3183).*
Mozdziak, and Petitte (2004, Developmental Dynamics, 229: 414-421).*
Murray, et al. (1999, Transgenic Animals in Agriculture, CAB International: Oxon, pp. 58-61).*
Schuster-Gossler, et al. (2001, BioTechniques, 31: 1022-1026).*
Wei (1997, Annu. Rev. Pharmacol. Toxicol., 37: 119-41).*
Tarrant et al. (2002, Molecular and Cellular Biology, 22: 5006-5018).*
Clouthier et al. (1998, Development, 125: 813-824).*
Kitayama et al. (2001, Biochemical and Biophysical Research Communications, 281: 1134-1140).*
Hammer et al. 1990, Cell, 6: 1099-1112.*
Cowan et al. 2003, Xenotransplantation, 10: 223-231.*
Hammer et al. 1986, J. of Anim. Sci., 63: 269-278.*
Moreadith and Radford, 1997, J. Mol. Med., 75: 208-216.*
Gerlai, 1996, Trends Neurosci, 19: 177-181.*
Schuster-Gossler et al. 2001, Biotechniques, 31: 1022-1026.*
D. Evans MJ, Kaufman M. Nature 292: 154-156 (1981).
Martin GR. Proc Natl Acad Sci USA 78: 7634-7638 (1981).
Smith AG. Annu Rev Cell Dev Biol 17: 435-462 (2001).
Lederman Band Burki K. Exp Cell Res 197: 254-258 (1991).
Le Fur Nathalie et al. Genomics 37: 245-248 (1996).
Potter H et al. Proc. Natl Acad Sci USA 81: 7161-7165 (1984).
Zimmer A et al. Nature 338: 150-153 (1989).
Joyner A et al Nature 338: 153-156 (1989).

* cited by examiner

*Primary Examiner*—Anne M. Wehbé
*Assistant Examiner*—Joanne Hama
(74) *Attorney, Agent, or Firm*—Rashida A. Karmali

(57) ABSTRACT

The present invention relates generally to the field of generating genetically modified C57 mice. More particularly, the present invention pertains to 1) blastocyst-derived mouse embryonic stem cell (ES) cell lines including, but not limited to, the IC1, IC2, IAC1, IAC2, IAC3, IAC4, IAC5, IAC6, IAC7 or IAC8 ES cell line, 2) to efficient methods of making genetically modified C57 mice by introducing the modified C57 ES cells into the mouse blastocysts of either the same mouse strain and/or color of albino C57 strain, or other C57 strain, to generate genetically modified novel, useful and hereto unknown models of C57 mice, and to methods for identifying the chimerism of chimeras which can be not known by coat color.

5 Claims, 19 Drawing Sheets

FIG. 5 ES cells are injected into blastocysts

Summary of germline transmission of C57 BL/6J-derived ES cell lines

| Construct | # Blastocysts Injected | Host Strain | Total # Born | # of PCR targeted | # Chimeras | # of pups 80% | # of neo-pups | # Germline Transmitters |
|---|---|---|---|---|---|---|---|---|
| GFP | 20 | C57 BL/6J | 8 | 5 | 1 | 34 | 7 | 1 |
| p53 | 20 | C57 BL/6J | 18 | 5 | 2 | 16 | 4 | 2 |
| p53+GFP | 20 | C57 BL/6J | 15 | 7 | 1 | 19 | 13 | 1 |

FIG. 9

"Black into black"

PCR identification of founders

"Black into black"

PCR identification. Lane 1, DNA ladder; lane 2, positive control (known neomycin positive DNA); lane 3, negative control (wild type DNA); lane 4-7, GFP founders 2-5; lane 8 and 9, p53 founders 1 and 2.

Southern blotting of founders and their offsprings

Southern blotting: Lane 1-5, P53 founder 1-5; lane 6-8, p53 F1 offspring 1-3.

"Black into black"

Summary of germline transmission of C57BL/6J-derived ES cell lines

| Construct | # Blastocysts Injected | Host Strain | Total # Born | # of PCR tested | # Chimeras | # of pups born | # of help+pups died | Germline Transmitters |
|---|---|---|---|---|---|---|---|---|
| p53 | 3 | Albino C57 | 3 | | 2 | 16 | 11 | 2 |

"Black into white"

FIG. 13

Chimeras from IC1 ES cells injected into albino C57 BL/6J blastocysts

ES cells

Chimeras

Blastocysts donor

"Black into white"

"Black into black"

Genetically modified ES cells (black)
↓
Injected into C57BL/6 (black)
↓
Germline transmission

Advantages

- Pure background
- High efficiency (100% germline transmission)
- Reduction in time and cost

FIG. 15

C57BL/6J-$Tyr^{c-2J}$-derived ES cell lines

"White into black"

FIG. 18

Results of germline transmission of C57BL/6J-$Tyr^{c-2J}$-derived ES cell lines

| Cell lines | # Blastocysts Injected | Host Strain | Total # Born | # Chimeras | # Chimeras tested | Germline Transmitters |
|---|---|---|---|---|---|---|
| IAC1 | 52 | C57BL/6J | 18 | 5 | 2 | 1 |
| IAC2 | 24 | C57BL/6J | 15 | 5 | 1 | |
| IAC5 | 20 | C57BL/6J | 8 | 2 | | |

A chimera produced from the injection of albino C57 ES cells into black C57 blastocysts

GENETIC MODIFICATION OF C57 MICE

1. FIELD OF INVENTION

The present invention relates generally to the field of generating genetically modified C57 mice. More particularly, the present invention pertains to methods for generating blastocyst-derived mouse embryonic stem cell (ES) lines, to methods for genetically modifying the ES cells, to the genetically modified novel ES cell lines invented, to methods for introducing the modified black C57 ES cells into the mouse blastocysts of either the same mouse strain and/or color of albino C57 strain, or other C57 strain, to generate genetically modified novel, useful and hereto unknown C57 mice.

2. BACKGROUND TO THE INVENTION

Mouse embryonic stem (ES) cells are continuous cell lines derived directly from the fetal founder tissue of the preimplantation embryo. They can be expanded in culture while retaining the functional attributes of pluripotent embryo cells. In particular, they can participate fully in fetal development when reintroduced into the embryo. The capacity for multilineage differentiation is reproduced in culture whose embryonic stem cells produce a wide range of well-defined cell types. Such pluripotent stem cells can constitute a renewable source of more differentiated cells that can be employed to replace diseased or damaged tissue by cellular transplantation.

Mouse ES cells were established from 129 strain mouse blastocysts in 1981, Evans M J, Kaufman M. Nature 292: 154–156 (1981); Martin G. R. Proc. Natl. Acad. Sci. USA 78: 7634–7638 (1981). They can be cultured and manipulated in vitro and then introduced back into the embryonic environment to differentiate into somatic and germ cell lineages even after transfection. The protocols for ES cell derivation include embryos at the expanded blastocyst stage being plated, either intact or following immunosurgical isolation of the inner cell mass (ICM) onto a feeder layer. Roberson E. J. Trends Genet. 2:9–13 (1986).

ES cells injected into host embryos give rise to mosaic mice known as chimeras. Male ES cells are injected into unsexed blastocysts. If the host embryo is female and the male ES cells make germ cells, the chimera will often be a fertile male. If the proportion of ES cell descendents in the coat of the animal is high, the probability that ES cells are represented in gametes is also high, since ES cells mix thoroughly with host cells early in embryogenesis. ES cells give rise to brown coat color because they are Aw/Aw (dominant White-bellied Agouti), and the host cells give rise to black coat color because they are a/a (recessive non-agouti). The ES cells are from the 129 strain of mice; the host embryos are from the C57BL6 strain of mice. If the chimeras are bred to a/a non-agouti mice (for example C57BL6 or Black Swiss), then any brown offspring (Aw/a) must have arisen from ES cell-derived gametes, and 50% of the brown offspring are expected to carry the knockout allele.

The differences in chimerism are due to different amounts of contribution of the ES cells to the Blastocysts. The better the ES cells do in the blastocyst the more cells of the embryo are derived from the ES cells. The most important lineage is the germ line, because that is the only way to pass on the genetic information to the next generation (germline transmission).

An important characteristic of ES cells is that even after extended propagation and manipulation in vitro, ES cells remain capable of re-entering embryogenesis, colonize the germ cell lineage into a chimera and generate functional gametes. Therefore, genetically modified mice can be derived from cultured ES cells. For example, the following types of genetically modified mice may be produced from genetically modified ES cells: 1) knockout mice in which a gene is dysfunctioned, 2) knockin mice in which a gene is introduced in a specific site of a gene of interest, 3) site-specific transgenic mice which is similar to the knockin but certain copies of the gene are merely introduced into a certain site. These are mosaics, with the exogenous gene in only a proportion of their cells and crossing these mosaic animals generates fully genetically modified offspring. 4) non-site-specific transgenic mice which is similar to the conventional transgenic mice but no pronuclear microinjection is employed.

Maintaining ES cell pluripotency and germline transmission are two most important factors to be addressed for generating genetically modified mice. For example, germline-competent ES cell lines require early passage of ES cells and addition of LIF in the culture medium, and conditions that contribute not only ES pluripotency but also germline transmission. The combination of ES cells and embryo is also a very important factor affecting germline transmission.

A large number of ES cell lines have been generated since 1981 and some of the commonly used ES cell lines include the CCE, HM-1, E14, AB1 and R1 lines, all these ES cell lines derived from 129-sub strains or 129 hybrids. Smith A. G, Annu Rev Cell Dev. Biol 17: 435–462, 2001. The preference for gene targeting in pure inbred lines has now dictated a demand for ES cell lines from various inbred strains, such as C57, Balb/c and DBA etc.

There is a special need for genetically modified C57 mice as experimental tools because in some medical fields, the C57 mice are more sensitive than other mice such as the 129 strain, e.g. in electrophysiology and neuroscience. For example, the C57 mice are more sensitive to tastants than 129 mice, and therefore, the C57 mice are preferred when studying taste transduction.

However, C57 ES cells are difficult to get germline transmission because they are much easier to differentiate than the 129 ES cells.

The chimerism of the chimeras is commonly evaluated by coat color, eg., if 129 ES cells are injected into black C57 blastocysts, the offspring, if chimeric, will be a black background (from C57 blastocysts), with agouti chimerism. The above example is the currently commonly used method for making genetically modified mice. If pure C57 background is preferred, normally researchers need to backcross the F1 offspring (50% 129; 50% C57) (which are commonly from the mating of chimeras with C57 mice, see FIG. 3) with C57 mice, this will take about 2 years after 8–10 generations of mating with C57 mice. This makes it very time-consuming to generate genetically modified C57 mice. The generation of gene-targeted mice via C57 ES cells has become an invaluable research tool. Balb/c mice and 129 mice were used to be host blastocysts for the C57 ES cells, the combination C57 ES cells with Balb/c blastocysts results in significantly higher frequencies of chimeras than the combination C57 ES cells with 129 blastocysts. Ledermann, B. and K. Burki, Exp. Cell Research 197:254–258 (1991). The main disadvantage of using Balb/c as donors is that it is difficult to get good quality and quantity of blastocysts from Balb/c mice because of their delayed embryonic development.

Some researchers have used albino C57 blastocysts (C57BL/6J-Tyr$^{c-2J}$) and introduced C57 ES cells into them with good result. C57BL/6J-Tyr$^{c-2J}$ strain has a white coat color but still C57 black background, it has a G to T base change at nucleotide 291 of the TyrC-2J allele and resulting in an amino acid change from arginine to leucine at residue 77 which lies in the highly conserved DDRE sequence. Le Fur et al, Genomics 37:245–248 (1996). The disadvantage is that albino C57BL/6J-Tyr$^{c-2J}$ mice are expensive and not available in large quantities for experimentation because only one vendor, the Jackson Laboratory, in Maine, provides this strain in limited quantity.

The present invention overcomes the disadvantages outlined above and provides methods for producing germline-competent C57 ES cell lines, and genetically modified (knockout, knockin or transgenic) C57 mice.

3. SUMMARY OF THE INVENTION

The present invention provides a method to establish germline-competent C57 ES cell lines from C57BL/6J delayed blastocysts.

The present invention also provides germline-competent C57 ES cell lines (black), including, but not limited to, the IC1, or IC2 ES cell lines.

The present invention also provides germline-competent albino C57 ES cell lines (white), including, but not limited to, the IAC1, IAC2, IAC3, IAC4, IAC5, IAC6, IAC7 or IAC8 ES cell lines.

The present invention also provides more efficient methods for generating genetically modified C57 mice, with various ES cell-embryo combinations.

The present invention further provides ES-cell-embryo combinations which efficiently get germline transmission, including C57 ES cells (black) introduced into black C57 blastocysts (black into black) or transfected black C57 ES cells into white C57 blastocysts (black into white). The invention also provides a novel method for evaluating the chimerism of black into black chimeras using PCR and Southern Blotting.

The invention provides a system for constructing an animal model for a disease involving a genetic defect by developing a non-human vertebrate animal ES cell line lacking the specific gene, developing a genetically modified mouse model whose genome comprises an introduced null mutation of the gene which said mouse exhibits, and using this model to screen therapeutics and other agents.

It is the object of the invention to provide a variety of genetically modified germline-competent C57 ES cell lines which are used for producing genetically modified C57 mice.

It is also the object of the present invention to provide more efficient methods for generating genetically modified C57 mice using different ES cell-embryo combinations.

It is also the object of the present invention to utilize the dual capacities of the ES cells for unlimited expansion and multi-lineage differentiation, to establish specific embryo-derived cell lines to investigate and manipulate specific gene functions—normal and abnormal, to understand the pathology of different diseases; and to provide large numbers of phenotypically defined ES cell types for screening of pharmaceutical compounds and toxicology testing.

It is also the object of the invention to create a renewable supply of cells for experimental use in cell replacement, tissue repair, and delivery of gene therapy in regenerative medicine using the murine model of stem cells.

4. BRIEF DESCRIPTION OF FIGURES

FIG. 1 depicts ES cells in context of mouse development, through a lineage diagram of mouse development with lineages colonized by ES cells from the epiblast. ES cells can produce hypoblast derivatives in vitro but rarely do so in vivo. Consistent with their epiblast origin, ES cells contribute poorly to extra embryonic endoderm and rarely if any, to trophoblast. However, consistent with their epiblast origin, ES cells behave relatively consistently in their ability to integrate into the embryo and produce viable chimeras epiblast derivatives—mesoderm, endoderm, and ectoderm and lineages developed thereof. Thus, genetic modification of ES cells, and their introduction into the same strain blastocysts can produce functional differentiated progeny in target tissues and organs mentioned above and provide novel viable chimeric C57 mice that are better, cost effective and more sensitive experimental models to study genetic modifications and abnormalities in specific diseases.

FIG. 2 depicts in detail the gene targeting procedure of the invention by homologous recombination, in mice. Gene targeting is a method of in vivo mutagenesis in which the mutation is introduced into a pre-selected endogenous gene. Gene targeting in ES cells (cloned DNA is transfected into embryonal stem cells) is particularly powerful because it can lead to the construction of an animal (transgenic animal) in which all nucleated cells contain a mutation at the desired focus. These animals can be bred to produce fully genetically modified offspring.

Briefly, genomic clones are isolated from mouse 129 strain. The genomic constructs are modified to mutate and single selection is carried out. The G418-resistant (G418R) ES clones are isolated. These are screened extensively to identify homologous recombinants using PCR and Southern Blots. Targeted ES cell cells are isolated, injected into C57BL/6 blastocysts, and transferred into the uterus of the foster mother. Three weeks later, pups are born and the chimeric offspring are identified by coat color. The male chimeras are out crossed and their germ line is determined using southern blot. The breeding of germ-line chimeras is continued and pups having the normal +/+, heterozygous +/– and homozygous –/– are the expected results.

FIG. 3 depicts the critical steps of gene targeting technology.

Mouse ES cells are derived from 3.5 day post-coitum embryos and arise from the inner cell mass of the blastocyst. The ES cells are cultured in vitro and retain the potential to contribute extensively to all of the tissues of a mouse, including germline, when injected back into a different coat color host blastocyst and reimplanted in a pseudopregnant mouse.

The developing embryo is a chimera: it contains two populations of cells derived from different zygotes, those of the blastocyst and the implanted ES cells. If the two strains of cells are derived from mice with different coat colors, chimeric offspring can easily be identified by coat color. For example, when modified ES cells from the 129 strain (agouti color) can be injected into blastocysts isolated from mouse strain C57B6/J (black) and then implanted into a pseudopregnant foster mother, chimeric mice containing two populations of cells are produced. Backcrossing of chimeras and subsequent inbreeding can produce mice that are heterozygous or homozygous (knockout) for the genetic modification. This is a lengthy and expensive process to produce these strains.

Figure 6:
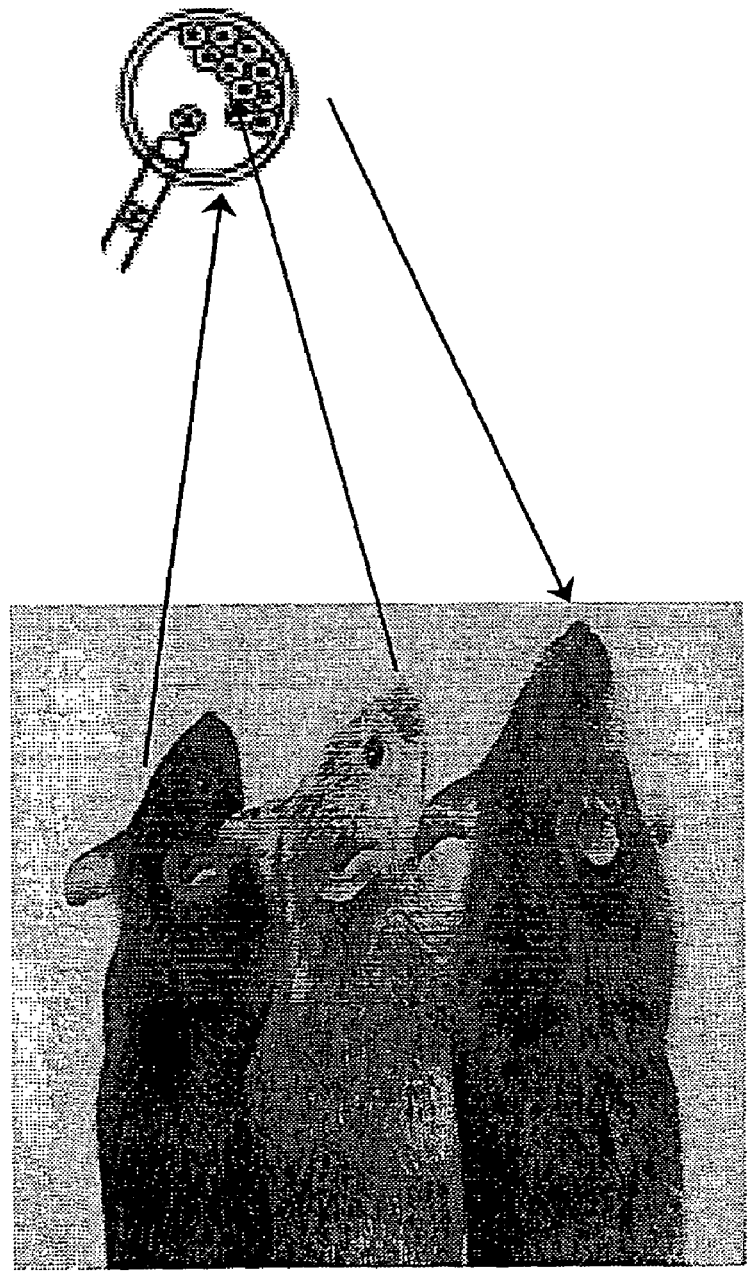

FIG. 6 describes the most commonly used "agouti into black" scheme in which genetically modified C57 ES cells were injected into black blastocyst donors to produce chimeras.

Figure 7:
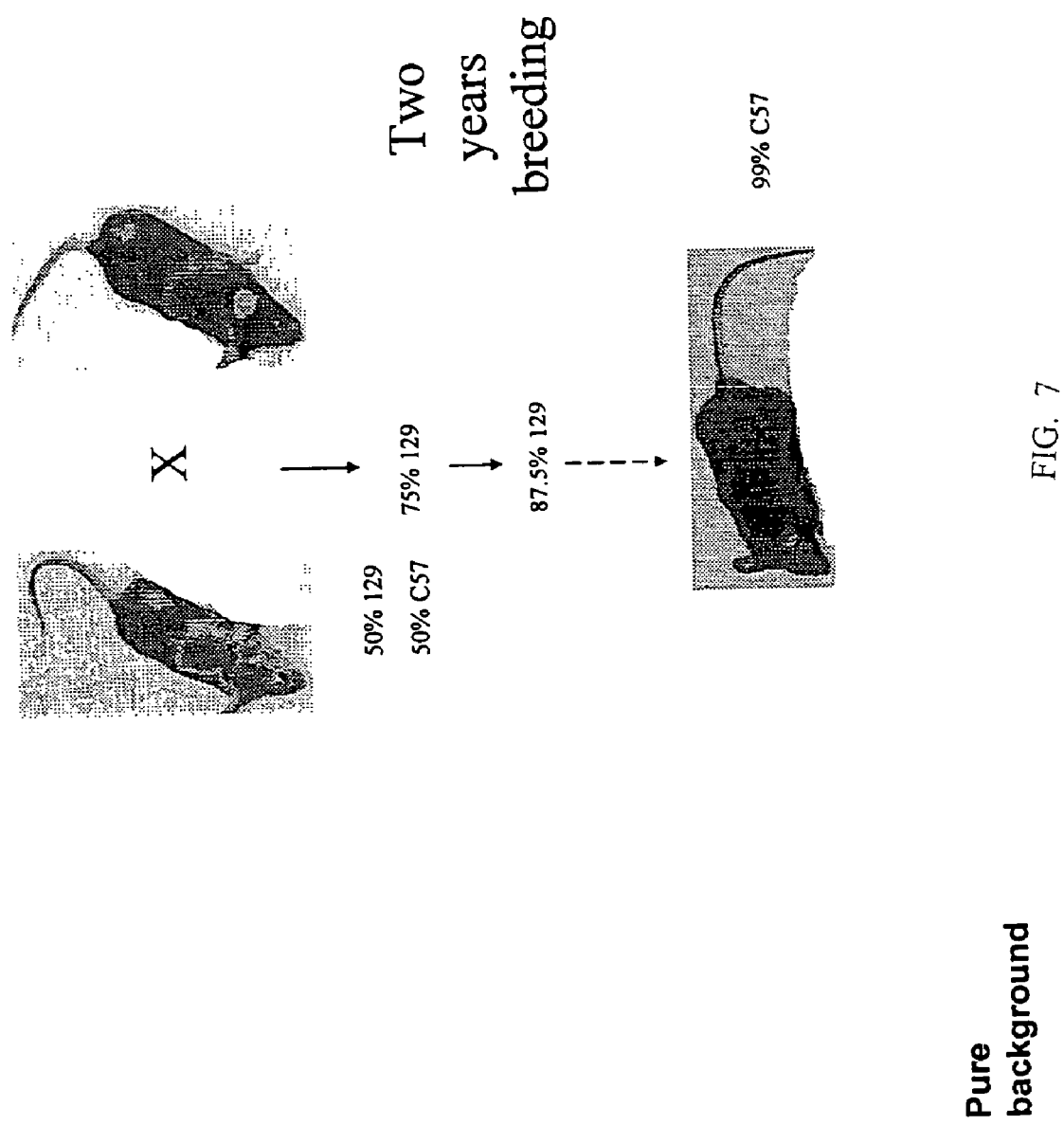

FIG. 7 describes the scheme of F1 offspring breeding over a longer period, for example, two years, to achieve a relatively pure C57 background.

Figure 8:
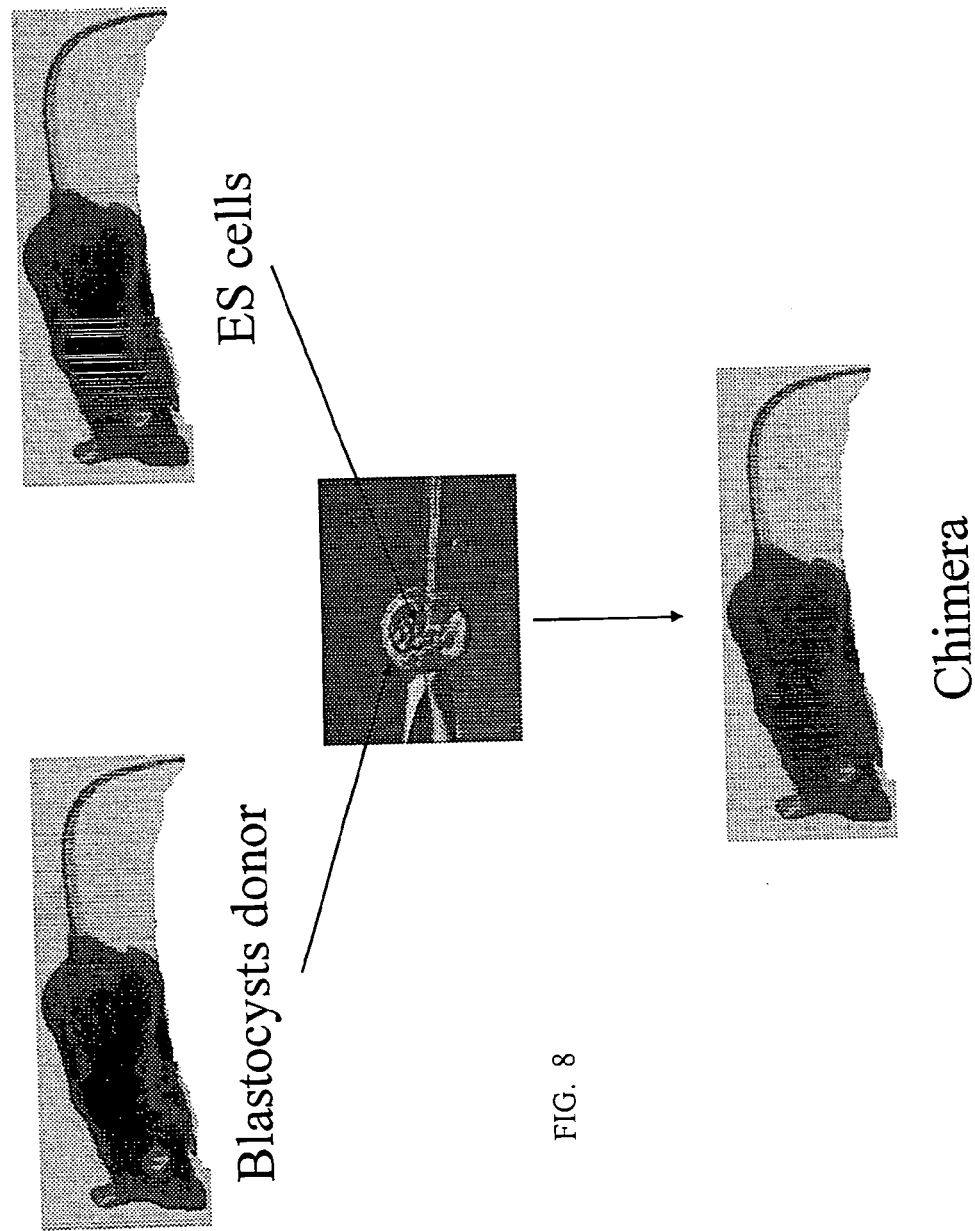

FIG. 8 describes the results if germline transmission of C57BL/6J-derived ES cell lines in the "black into black" scheme.

FIG. 9 describes the results of germline transmission of C57BL/6J-derived ES cell lines (black into black).

Figure 10:
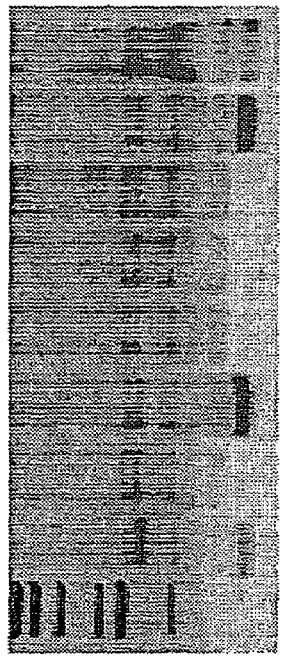

FIG. 10 describes the results obtained by PCR identification of F1 offspring genotypes of chimeras obtained from IC1 ES cells (black) injected into black C57BL/6J blastocysts. Lane 1 is the DNA ladder, lane 2 is the positive control, lane 3 is the negative control, lanes 4–7 are GFP founders 2–5, and lanes 8 and 9 are P53 founders 1 and 2.

Figure 11:
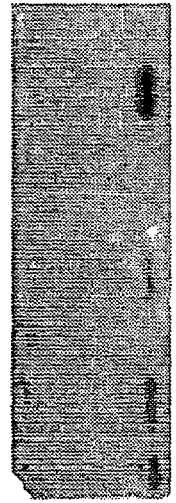

FIG. 11 describes the results obtained by Southern Blot identification of F1 offspring genotypes of chimeras obtained from IC1 ES cells (black) injected into black C57BL/6J blastocysts.

Lanes 1–5 represent P53 founders; and lanes 6–8 represent P53 F1 offspring 1–3.

Figure 12:
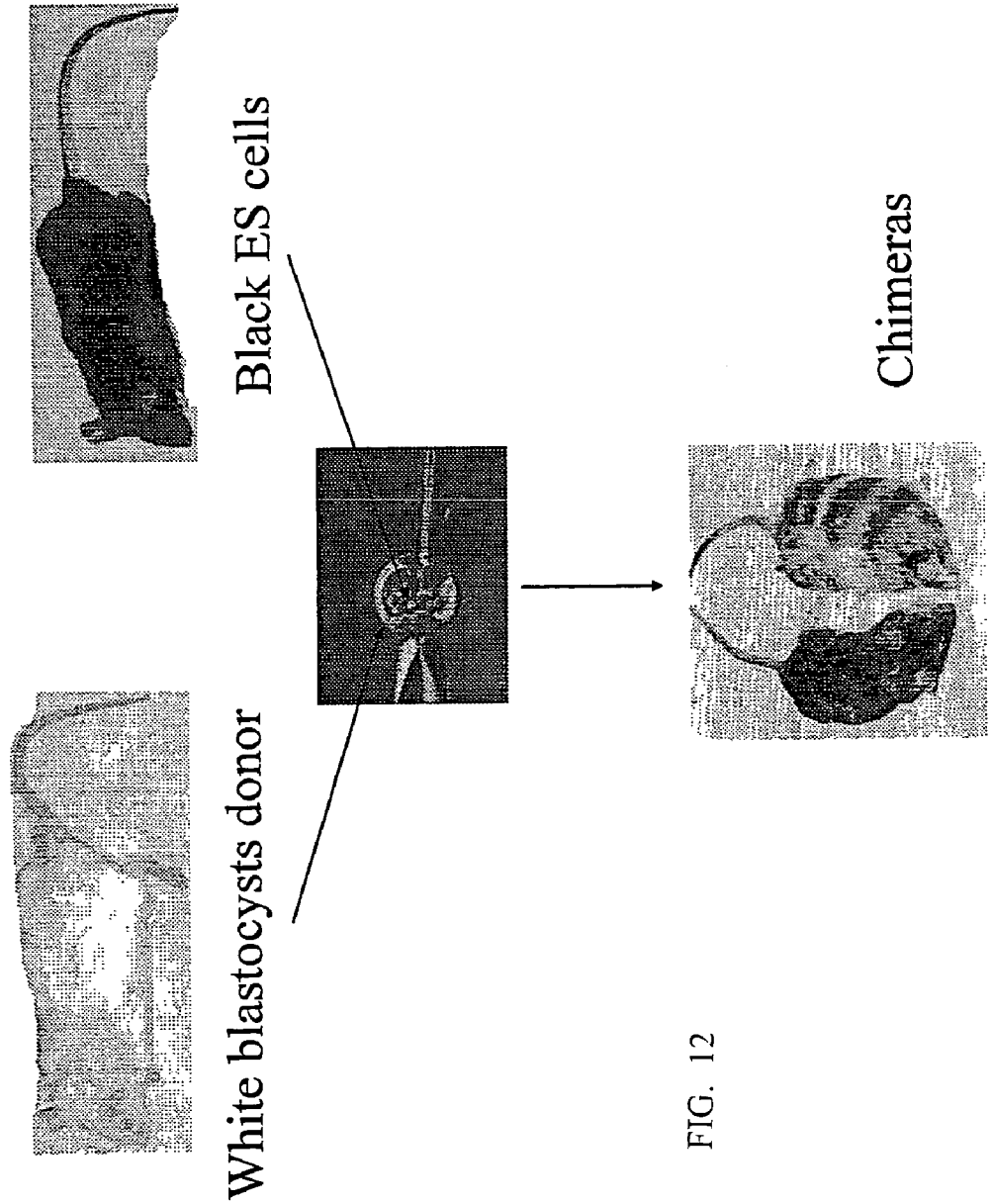

FIG. 12 describes the "black into white" scheme in which genetically modified C57 ES cells (black) were injected into white blastocyst donors (C57BL/6J-$Tyr^{c-2J/+}$) to produce chimeras.

FIG. 13 describes the results of germline transmission of C57BL/6J-derived ES cell lines (black into white).

Figure 14:
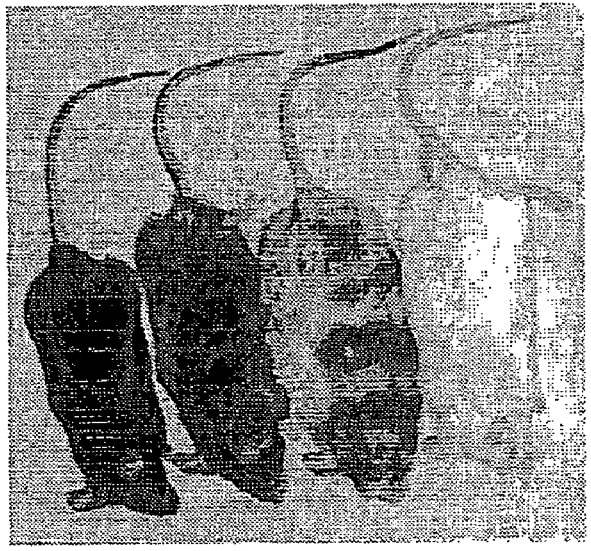

FIG. 14 shows chimeras from IC1 ES cells (black) injected into albino C57BL/6J blastocysts including from the top to bottom, $1^{st}$ mouse black C57 (C57BL/6J), $2^{nd}$ mouse 80–90% chimera, $3^{rd}$ mouse 50% chimera, and the $4^{th}$ mouse albino C57 mouse (C57BL/6J-$Tyr^{c-2J/+}$)

FIG. 15 describes summarized the method to produce same strain germline transmission, which can be "black in black", "white in white" or "agouti in agouti", heretofore, never done; and lists some of the advantages of the invention.

Figure 16:
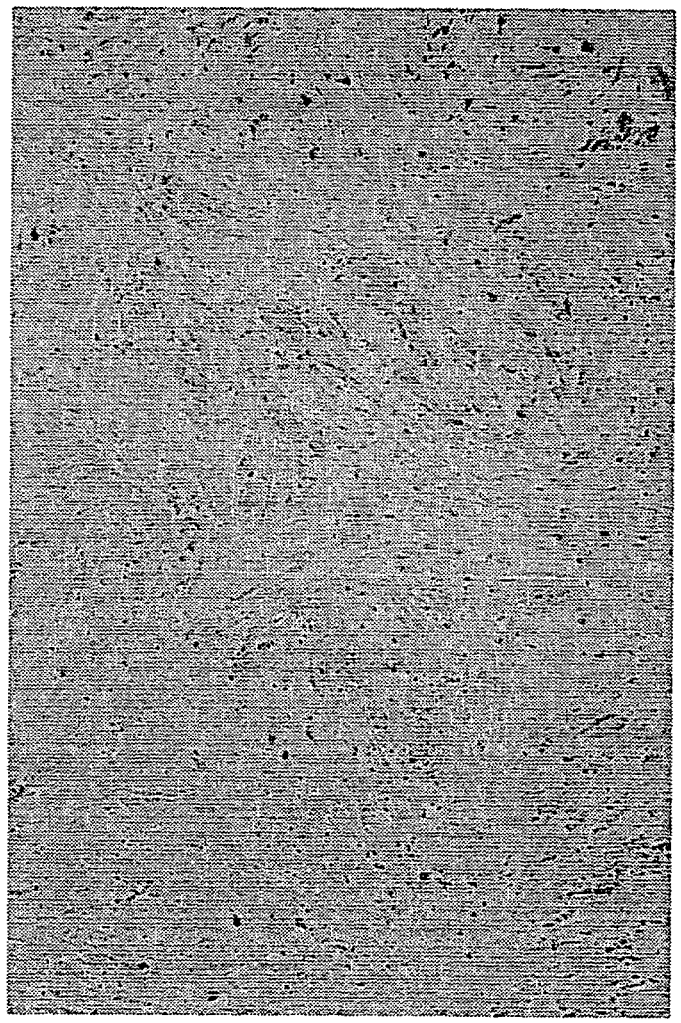

FIG. 16 depicts the culture of albino C57BL/6J-$Tyr^{c-2J}$-derived ES cells (white) in "white in black" scheme.

Figure 17:
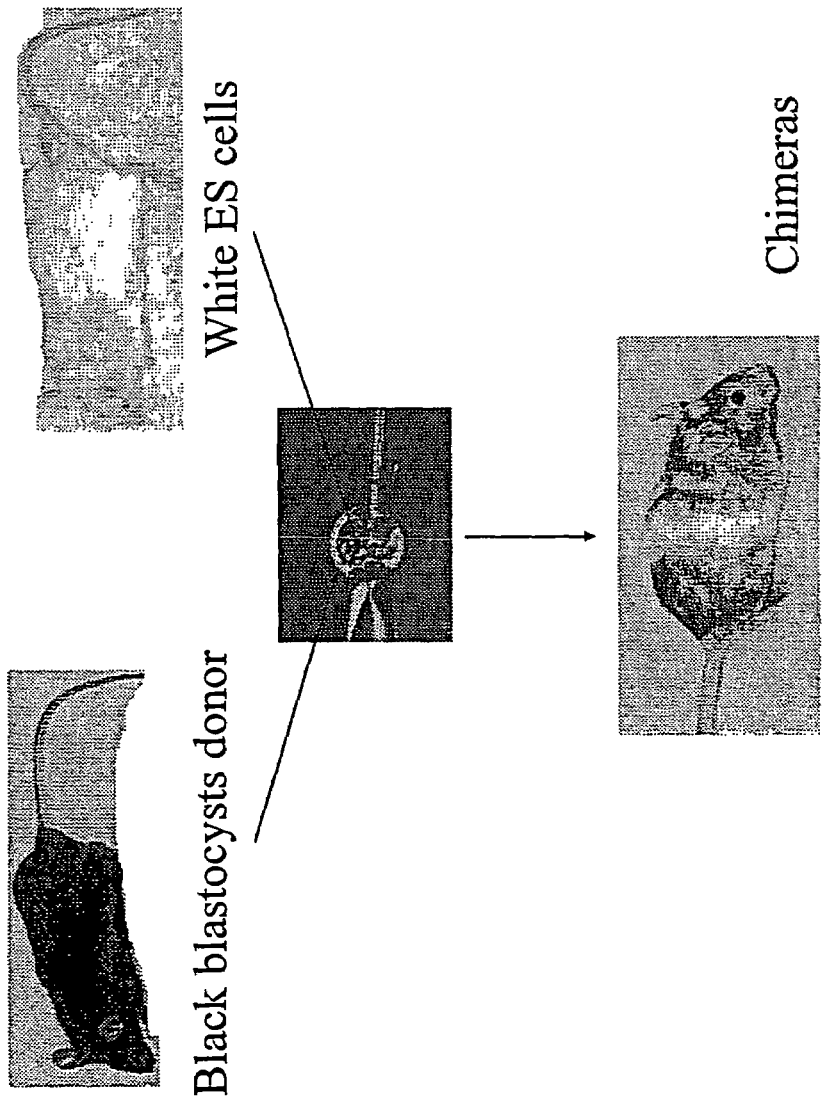

FIG. 17 describes the "white into black" scheme in which the albino C57 ES cell lines were injected into Black C57 blastocyst donors.

Figure 1:
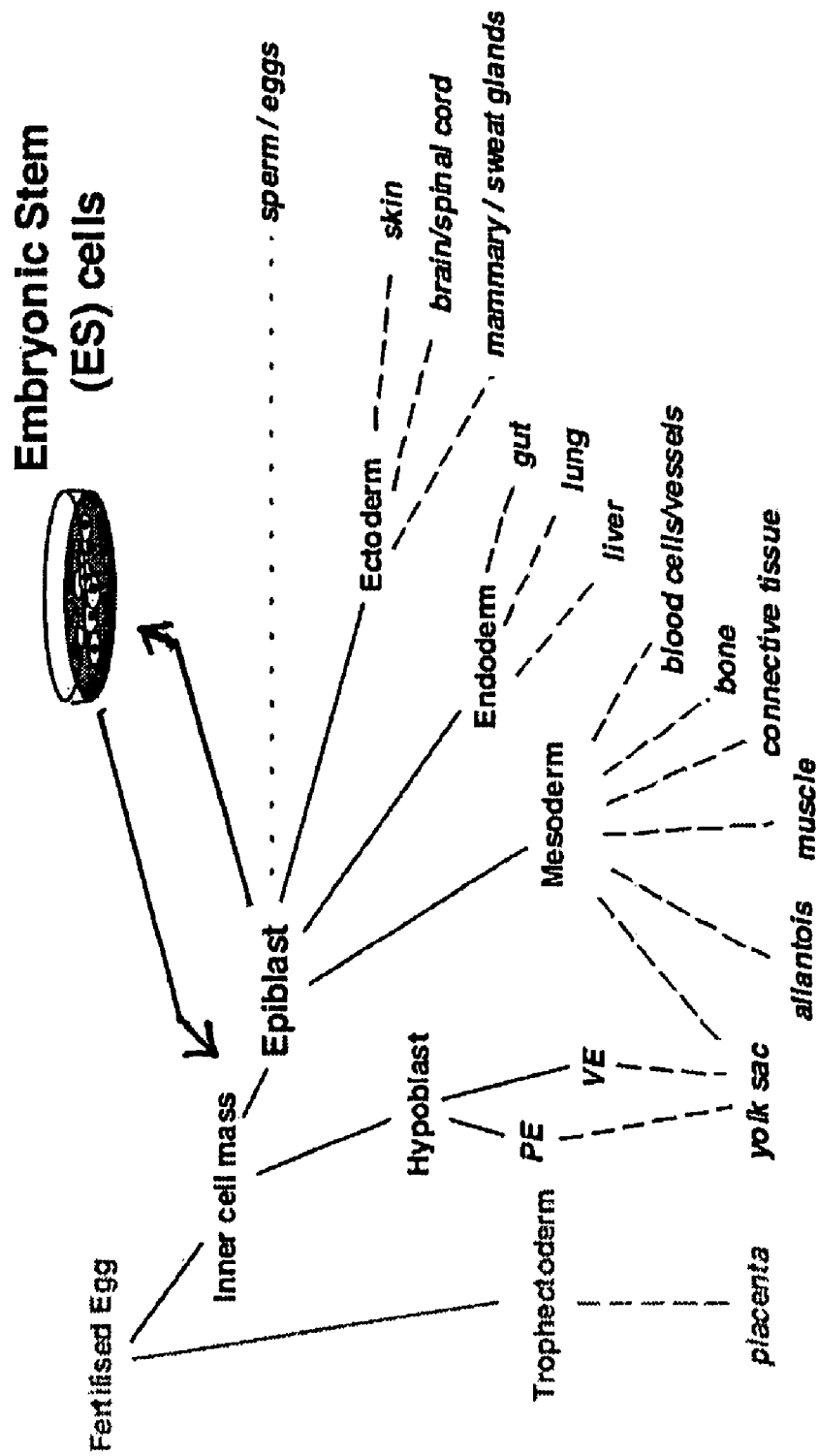
Figure 2:
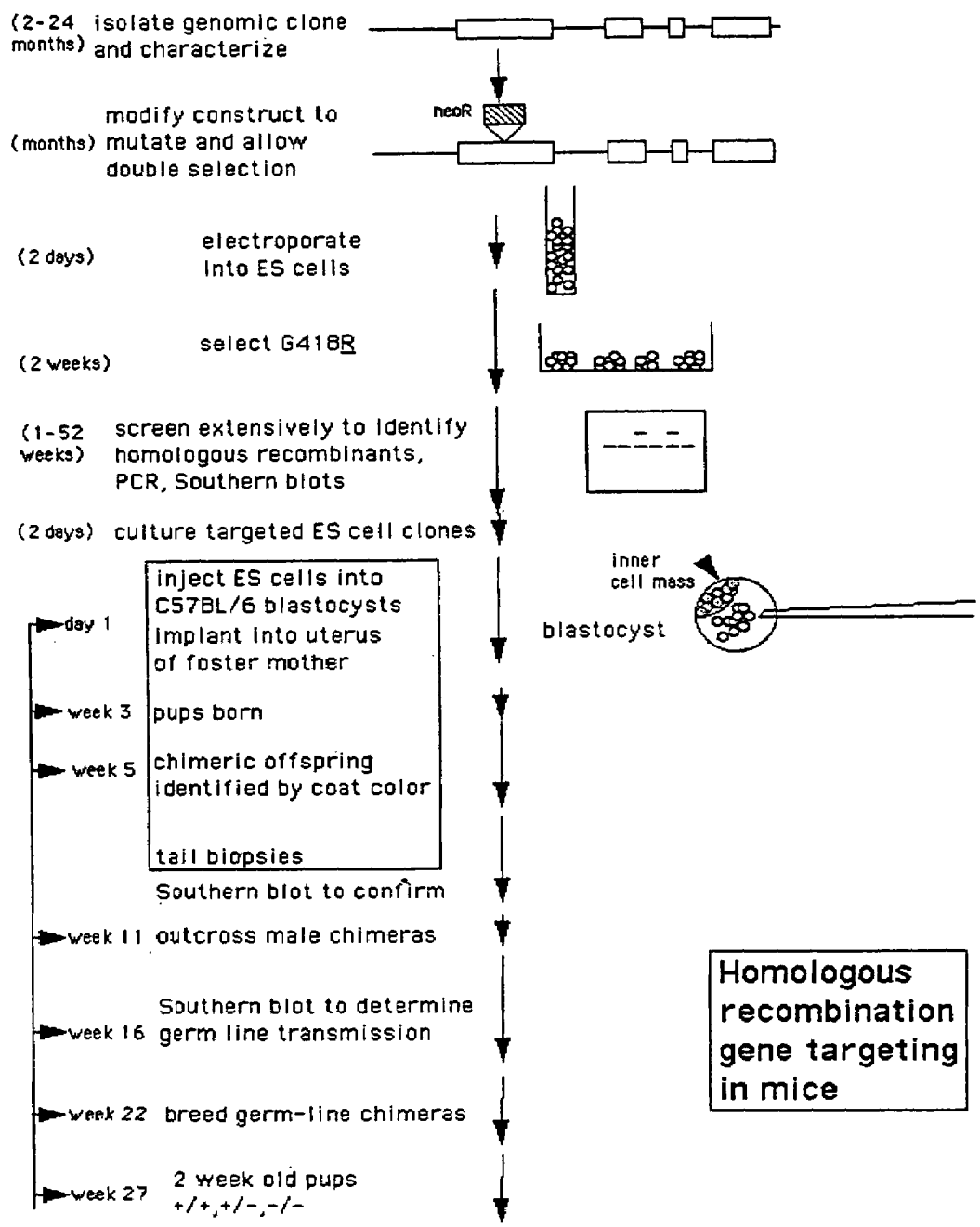
Figure 3:
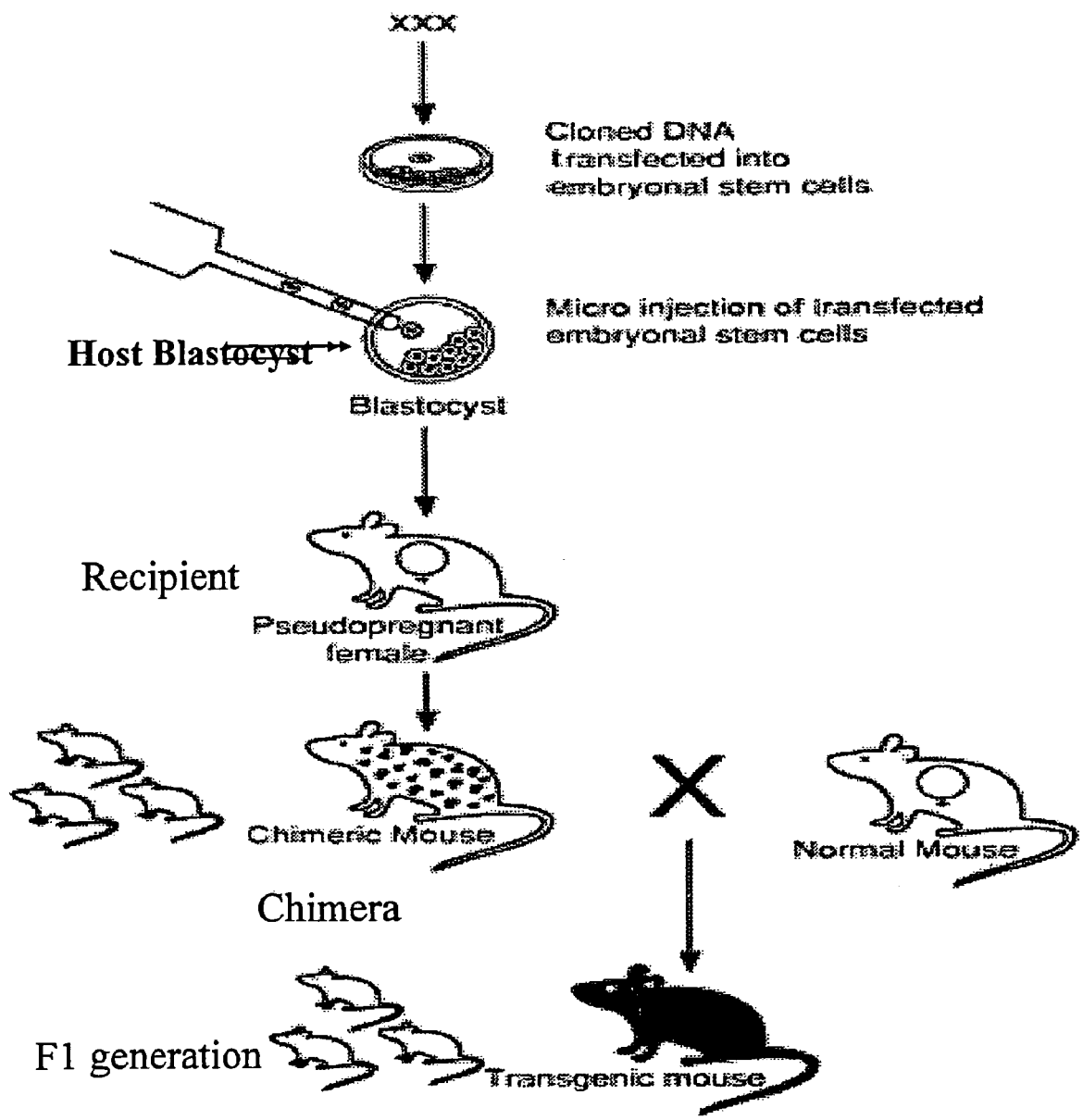
Figure 4:
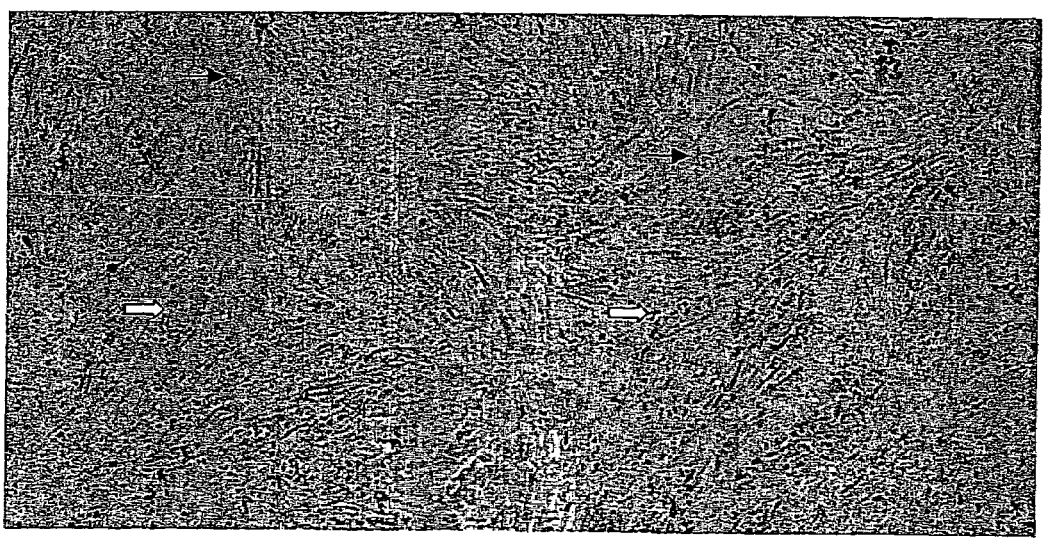
FIG. 4 shows the growth of ES cells in culture. Hollow arrows show the ES colonies and the single filled arrows show the fibroblast-like feeder cells.
Figure 5:
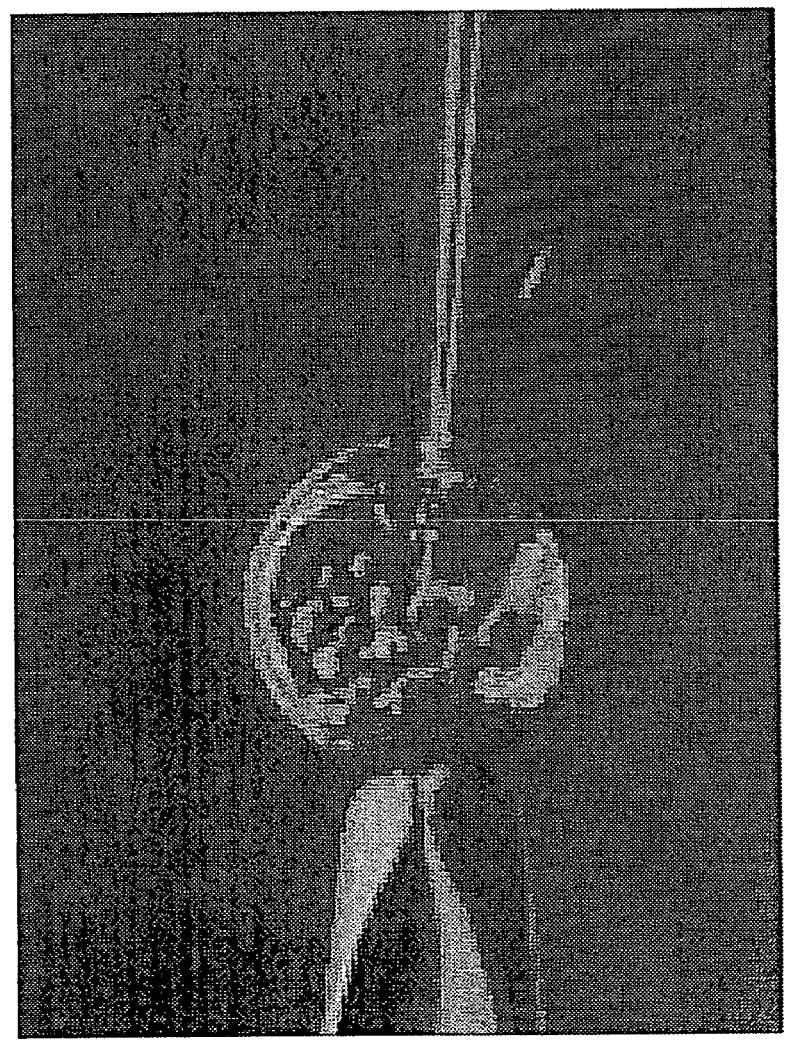
FIG. 5 depicts a diagram a technique showing ES cells being injected into blastocysts.

FIG. 18 describes the results of germline transmission of C57BL/6J-$Tyr^{c-2J}$-derived ES cell lines (white) from three albino C57 ES cell lines into black C57 blastocytes and summarizes the results of experiments done on germline transmission of C57BL/6J-$Tyr^{c-2J}$-derived ES cell lines. Results obtained from ongoing experiments show that germline transmission occurred with the chimeras derived from IAC1 cell line (white), shown above in FIG. 4.

Figure 19:
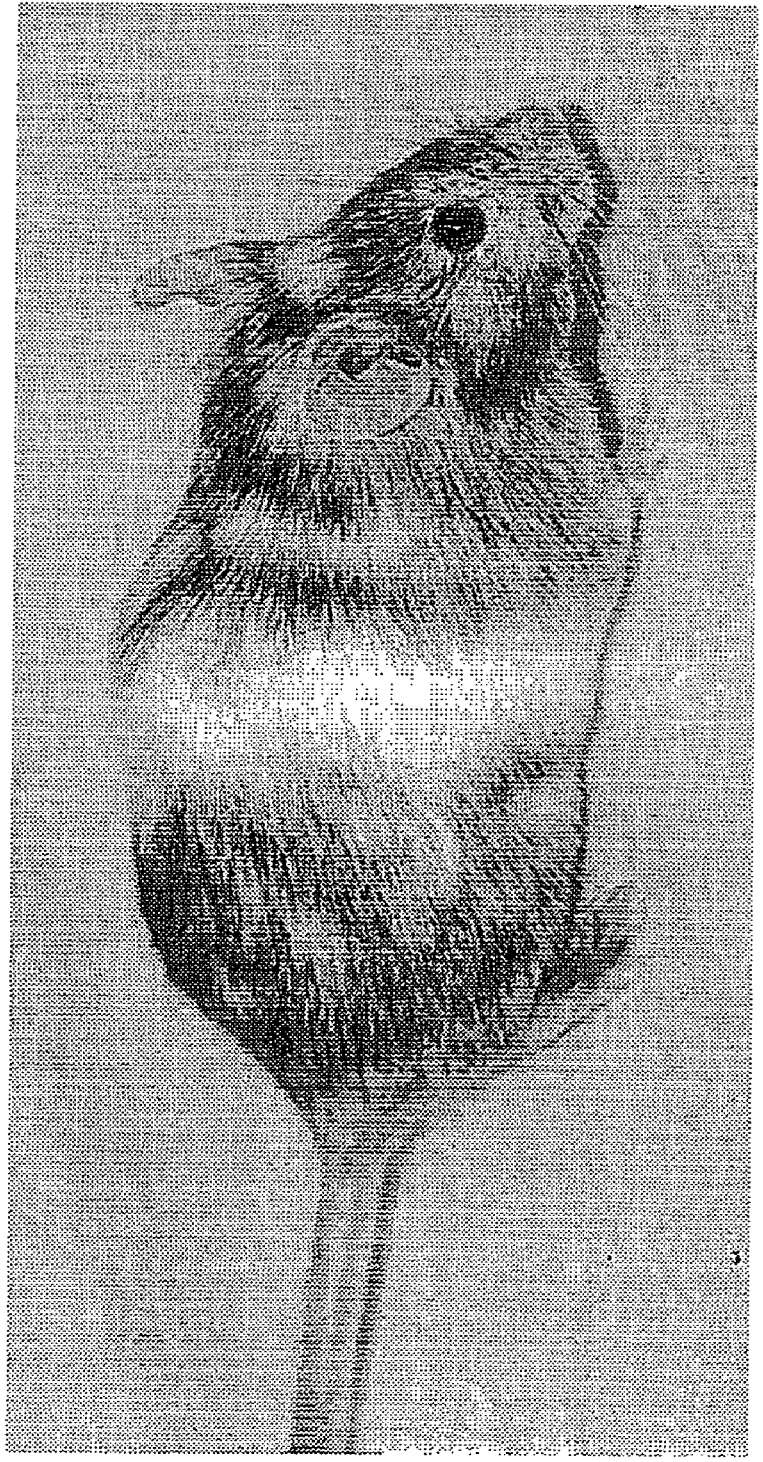

FIG. 19 shows a chimeria prepared from albino C57 ES cells injected into black C57 embryos.

5. DETAILED DESCRIPTION OF THE INVENTION

Gene targeting and transgenesis represent the two most direct and powerful approaches for analyzing gene function in higher organisms. Further, both approaches can be exploited in order to derive strains of animals with properties that are desirable either for industry or for medicine.

Transgenesis defines any process that involves the transfer of a gene from one species to another. However, the term is often used in order to define the insertion in the mouse genome of modified mouse genes in order to dissect gene function. In principle (and in practice), transgenes can be directed to the germline using the ES cell technology. However, another approach, namely direct microinjection of the DNA encoding the gene under study in the pronucleus of a fertilized egg has been extensively used to produce gain of function mutations and is still the method of choice when lines expressing the transgene in high copy numbers are sought.

A wide variety of vectors has been employed for transgenic studies and two classes will be recollected here. In the first one regulatory sequences (for example promoter enhancer elements) of the gene under study are used to direct the expression of a reporter gene, for example the gene encoding bacterial b-galactosidase for which simple and relatively sensitive histochemical detection exist. These studies can establish directly in vivo the stages and the tissue domains in which the gene under study is expressed.

A second class of transgenes involves the use of one of several well characterized promoters in order to drive the expression of the gene under study and alter the physiological pattern of gene expression. Typically these experiments lead to over and/or mis-expression of the gene and they enable the analysis of the ensuing phenotype. In a significant development of the latter approach, inducible or lineage-restricted promoters can be used in order to achieve further control of the pattern of expression of the gene.

The pronuclei of fertilized mouse eggs can be most easily injected at the one-cell stage when they are at their maximum size. For most strains of mice this is between 24 and 28 hours after mating. Females used for the generation of fertilized eggs for pronuclear injection are typically induced to "superovulate", ie to ovulate a number of eggs higher than physiological. Superovulation is achieved pharmacologically by injecting the mice with pregnant mare's serum (to mimick follicle-stimulating hormone, FSH) 48 hours before injection of human chorionic gonadotropin (hCG, to mimick luteinizing hormone).

For microinjection, eggs are recovered from the oviduct and treated with hyaluronidase in order to free the egg from the cumulus cells and are transferred to a Petri dish where they are injected. Either of the two pronuclei can be injected. However, the male pronucleus is larger and is injected in preference. After injection eggs are either transferred directly into the oviduct of a 0.5 dpc foster mother or cultured in vitro to the two-cell stage (overnight) and transferred the following morning.

Gene targeting involves engineering a mutation in a pre-selected gene within an intact cell. The mutation may result in inactivation of gene expression (a "knockout" mutation), or altered gene expression, and so can be useful for studying gene function, e.g., in the apolipoprotein E deficient (Apo-E KO) mice, the melanoma and immunotherapy model, etc.

In addition, the same method can be used to "correct" a pathogenic mutation by restoring the normal phenotype, and so has therapeutic potential.

Gene targeting typically involves introducing a mutation by homologous recombination a cloned gene (or gene segment) which is closely related in sequence to an endogenous gene is introduced into the cells, and the cells are selected in which homologous recombination has occurred between the introduced gene and its corresponding chromosomal homolog. An important application of the technique is in mouse ES cells. Once a mutation has been engineered into a specific mouse gene within the ES cells, the modified ES cells are injected into the blastocyst of a foster mother and eventually a mouse can be produced with the mutation in the desired gene in all nucleated cells. However, homologous recombination in mammalian cells is very rare.

The invention also provides a variety of C57 ES cell lines including, but not limited to, IC1, or IC2.

The invention also provides a variety of C57 ES cell lines including, but not limited to, IAC1, IAC2, IAC3, IAC4, IAC5, IAC6, IAC7, or IAC8.

The invention also provides a screening assay method to evaluate the chimerism of the germlines generated.

The invention also provides methods for generating genetically modified C57 mice using the genetically modified ES cells (IC) and injecting them into C57 blastocysts (black into black) or injecting black C57 ES cells into white C57 blastocysts (black into white).

The invention also provides methods for making a homozygous knockout mouse whose genome compromises a disrupted genetic defect, comprising the steps of a) introducing the neo gene by homologous recombination in mouse ES cells, b) introducing said ES cells into a mouse blastocyst and transplanting said blastocysts into a pseudopregnant mouse, c) allowing said blastocyst to develop into a chimeric mouse and screening the chimerism by PCR and Southern Blot, d) breeding said chimeric mouse to produce F1 offspring and e) screening said offspring to identify a heterogenous transgenic knockout mouse whose genome comprises a marker gene, such as the neo gene, and wherein said mouse exhibits chimerism of coat color that may or may not be visible.

The present invention also pertains to animal models of human disease because they allow detailed examination of the pathophysiological basis of a disease and offer a front line testing system for studying the efficiency of novel treatments.

Most of the ES cell lines currently in use in a number of laboratories throughout the world are derived from the 129 mouse strain (129/Sv) which is homozygous, wild-type at the agouti locus. Non agouti offspring can be distinguished by eye at approximately 1 week. The primary source of ES cells are normal 3.5 dpc blastocysts. These are collected from the uterine horns and placed in culture on "feeder" layers of primary, embryo fibroblasts or suitable fibroblast strains (such as the STO). These feeder cells are irradiated or treated with mitomycin C (an inhibitor of DNA synthesis) in order to prevent growth of feeder cells. After 1–2 days in culture the cells from the inner cell mass start to divide and after another day or two the clump of cells derived from the inner cell mass is disaggregated with trypsin-EDTA and transferred to a new dish. Colonies are inspected and those with stem-cell-like morphology are recovered and propagated with regular subculturing in medium that minimize the differentiation of the cells.

In most instances, that is except in cases in which gene trap approaches are used, gene targeting in ES cells by homologous recombination relies on some knowledge of the gene under study and gene targeting is achieved by introducing a targeting vector in the form of naked DNA in the ES cells by electroporation. The simplest targeting vectors consist of two gene fragments (of at least several hundred, typically of several thousand nucleotides) separated by an unrelated sequence that may replace the corresponding gene sequence through a double crossover event. It is essential that the unrelated sequence contains a genetic marker (for example the gene encoding neomycin phosphotransferase which, once expressed, confers resistance to neomycin or neomycin analogues in order to select for vector integration (whether random or homologous).

For blastocyst injection with targeted ES cells, normal 3.5 dpc blastocysts are collected and cultured briefly to promote expansion. For microinjection, individual blastocysts are collected on a holding pipette and positioned such that the inner mass is located away from the injection needle. ES cells (10–15) are injected in the blastocoel cavity and the blastocyst is transferred to a Petri dish. For re-implantation, several blastocysts (up to 8) are transferred in the uterus of a foster mother obtained by mating to a vasectomized male 2.5 to 2.5 days before transfer.

Although most mouse knockouts generated based on 129 genetic background, C57 is the preferable strain over 129 strain for behavioral and immunological studies. Because the inbred 129 substrains have been characterized as poor learners, especially 129/SvEvTac mice which are commonly used for establishing 129 ES cell lines, perform poorly on many behavioral tasks, resulting in potential interpretational difficulties. Ballogh S. A. Brain Research. 863:38–48 (1999). Although genetically modified C57 mice are highly in demand, most C57 ES cell lines and commonly used ES cell-embryo combination give inefficient results. The production of genetically modified mice has been difficult for the researchers. The blastocyst donor is commonly taken from Balb/c mice. However, it is very difficult to get good and enough amounts of blastocysts from Balb/c mice because of their delayed embryonic development. When co-isogenic host blastocysts from white C57BL/6J-Tyr$^{c-2J}$ are used, the results are good but these albino white C57BL/6J are expensive and not available for large numbers of mice needed for experimentations. Also, most facilities do gene targeting with 129 ES cells and using black C57 mice as blastocyst donors. Using albino C57 mice as blastocyst donors increases the cost because a different space facility has to be set up for the albino C57 mating. To improve the efficiency of generating genetically modified C57BL/6 mice, the present invention developed a series of C57 ES cell lines, and a series of ES cell-embryo combinations to generate genetically modified C57 mice, including but not limited to, black to black, black to white, white to black or agouti to black.

The advantages of the present invention are that these new C57 ES cell lines and ES cell-embryo combinations provided novel and efficient experimental approaches, which have not been available thus far because 1) there are very few C57 BL/6J ES cell lines available, 2) it is hard to find proper host blastocysts for the C57 ES cells.

Injecting black C57 ES cells into black C57 blastocysts make the identification of chimerism difficult. Injecting black C57 ES cells into white C57 blastocysts overcomes the above disadvantages. However, expensive albino C57 mice and another space for albino C57 mice are the new drawbacks. That is why in the present invention the albino C57 ES cell lines were established for the final resolution of all above problems. The present invention also provides albino C57 ES cells generated from albino C57BL/6J-Tyr$^{c\text{-}2J}$, so that these albino C57 ES cells (black) may be injected into blastocysts from black C57BL/6J mice (white into black).

The following list of terms as used herein, is intended to supplement the descriptions above, will be useful in understanding the present invention:

ES cells: Embryonic Stem Cells (ES cells) isolated from early stage embryos are pluripotent stem cells with the potential to make any differentiated cell in the body.

Coat color and chimeric mice (chimeras): Coat color is determined by one gene product that comes in many forms. If the ES cells were derived from a pure breeding brown mouse, and the blastocysts were from a pure breeding black mouse. The gene encoding the brown hair is dominant to black. Therefore the chimeric mice have a combination of brown and black hair. ES cells injected into host embryos give rise to mosaic mice known as chimeras. The differences in chimerism are due to different amounts of contribution of the ES cells to the blastocysts. The better the ES cells do in the blastocyst, the more cells of the embryo are derived from the ES cells. The most important lineage is the germ line, because that is the best way to pass on the genetic information to the next generation.

Vectors for gene targeting in ES cells: In most instances, that is except in cases in which gene trap approaches are used, gene targeting in ES cells by homologous recombination relies on some knowledge of the gene under study and gene targeting is achieved by introducing a targeting vector in the form of naked DNA in the ES cells by electroporation.

Homologous Recombination: The term "homologous recombination" refers to the process of DNA recombination based on sequence homology. The term embraces both crossing over and gene conversion. Cellular recombination enzymes are believed to be involved in the process of recognizing sequence identity between distinct nucleotide sequences.

Gene Targeting: Homologous recombination between two DNA sequences, one of which is located on a chromosome and the other of which is not.

Selectable Marker: A gene, the expression of which allows cells containing the gene to be identified on a particular medium. A selectable marker can be one that allows a cell to proliferate on a medium that prevents or slows the growth of cells without the gene. Examples include antibiotic resistance genes and genes which allow an organism to grow on a selected metabolite. Alternatively, the gene can facilitate visual screening of transformants by conferring on cells a phenotype that is easily identified. Such an identifiable phenotype may be, for example, the production of luminescence or the production of a colored compound, or the production of a detectable change in the medium surrounding the cell.

EXPERIMENTAL

A. General Methods: Generally, the nomenclature and standard laboratory procedures with respect to establishment of ES cell lines and gene targeting technology can be found in Hogan, B. et al., Manipulating the mouse embryos, Cold Spring Harbor Laboratory, Cold Spring Harbor, N.Y. (1986) (hereinafter "Hogan").

B. Preparation of the Targeting DNA: Modification of the targeting DNA depends on two basic considerations: firstly, what modifications are desired in the target DNA; secondly, whether selectable sequences should be included as an aid in isolating transgenic clones or homologous recombinants.

C. Introduction of the DNA into the ES Cells: Any technique that can be used to introduce DNA into the animal cells of choice can be employed. Electroporation has the advantage of ease and has been found to be broadly applicable, but a substantial fraction of the targeted cells may be killed during electroporation. In this technique, animal cells are electroporated in the presence of DNA containing the targeting construct. Electrical impulses of high field strength reversibly permeabilize biomembranes allowing the introduction of the plasmids. The pores created during electroporation permit the uptake of macromolecules such as DNA. Procedures are described in, e.g., Potter, H., et al., Proc. Nat'l. Acad. Sci. USA 81:7161–7165 (1984).

D. Identification for Integration Events: In some situations, the gene targeting event itself results in a selectable phenotype, in which case the targeted cells can be screened directly for homologous recombination. For example, disrupting the gene hprt results in resistance to 6-thioguanine. In many cases, however, the targeting does not result in such an easily selectable phenotype and, if a low efficiency transformation technique such as calcium phosphate precipitation is being used, it is preferable to include in the targeting DNA construct a selectable marker such that the stable integration of the targeting DNA construct in the genome will lead to a selectable phenotype. For example, if the targeting DNA contains a neo gene, then selection for integrants can be achieved by selecting cells able to grow on G418. The relative frequency of targeting to a gene may be further improved by using a selectable marker which lacks its own promoter, since the likelihood of adequate expression of the selectable marker is greater where integration into a gene has occurred than for integration into the large parts of the genome that are believed to be transcriptionally quiescent.

E. Isolation of genetically modified ES colonies: The standard approach for confirming that a cell has undergone a homologous recombination event is to isolate genomic DNA and perform a Southern hybridization analysis to demonstrate that genomic DNA fragments hybridizing with a labelled probe of the target DNA have been rearranged because of the modification of the target DNA. Another approach is to utilize the polymerase chain reaction to screen the cells for homologous recombinants. See, e.g., Zimmer, A., et al., Nature, Vol. 338, pp. 150–153 (1989); and Joyner, A., et al., Nature, Vol. 338, pp. 153–156 (1989).

F. Production of Genetically modified Animals: Genetically modified embryonic stem cells can be injected into the cavity of a blastocyst and grown in the uterus of a pseudopregnant female. The resulting chimeras can be bred in order to obtain non-chimeric animals which have received the modified genes through germ-line transmission.

6. EXAMPLES

Example 1

Generation of Genetically Modified Black C57 ES Cells and Albino C57 ES Cells

C57BL/6 mice were obtained from Taconic. C57BL/6J-Tyr$^{c\text{-}2J}$ (TyrC-2J) were obtained from Jackson Lab. Embryos were flushed from the uterus of C57BL/6 and C57BL/6J-Tyr$^{c-2J}$ with FHM medium (Specialty Media) on the fifth day after natural mating. Well developed blastocysts were transferred to ES medium of 96 well plate with gamma-irradiated mouse embryonic fibroblasts as feeder layers and late developed embryos were put into the KSOM medium (Specialty Media). ES cell medium contains 15% FBS (HyClone), 1 mM non-essential amino acids (GIBCO), 0.1 mM 2-mercaptoethanol (GIBCO), 1000 units/ml Leukemia—inhibitor factor (LIF) (Chemicon:ESG 1107). All embryos in KSOM were transferred to ES medium four days later.

Two black C57 ES cell lines (IC1 and IC2) were established.

To generate genetically modified C57 ES cell lines, black C57 ES cells were electroporated by two of different constructs containing neo gene cassette. In the first one, the new cassette was inserted into partial cloned p53 gene and in the second construct, the neo gene cassette was linked to GFP gene. G418-resistant colonies were picked up and expanded for the further identification and microinjection.

Eight albino C57 ES cell lines from C57BL/6J-Tyr$^{c-2J}$ (IAC1-IAC8) were established.

IC1 and ICA1 have been deposited with The American Type Culture Collection, Manassas, Va 20108.

Example 2

Generation of "Black into Black Chimeras"

Blastocysts were harvested by flushing uterus of 3.5 dpc black C57BL/6J mice. Genetically modified black C57 ES cells were injected into black blastocyst donors to produce a black germline transmission. There is no record in prior act of the above procedure. Since color changes are not helpful in detecting the chimeras, PCR and Southern Blot techniques were used to evaluate the chimeras. Results are given in FIG. 10 and FIG. 11, respectively. The advantages of the above technique are pure background, high efficiency (100%) germ line transmission and reduction in cost and time for producing the animals for use in experimentation. FIG. 8 summarizes the results of germline transmission of the black into black scheme.

Example 3

Generation of "Black into White" Chimeras

Genetically modified C57 ES cells (black) were injected into albino C57BL/6 (white) blastocyst donors to produce chimeric germline transmission. FIG. 12. The only record in prior act of injecting ES cells (black) into albino C57BL/6 (white) is by Schuster-Gossler, K et al Biotechniques 31:1026–1034 (2001). However, these authors used wild type ES cells (black) and not genetically modified ES cells (black). FIG. 12 and FIG. 13 describe the results for chimeras and germline transmission for above experiments.

Example 4

Generation of "White into Black Chimeras"

Three of the C57 ES cell lines were injected (IAC1, IAC2 and IAC5). FIG. 18. Chimeras were obtained. FIG. 17 describes the novel and useful "white into black" scheme in which the albino C57BL/6 ES cells (white) were injected into C57Bl/6 (black) blastocysts. A chimeric germline transmission was generated. There is no corresponding prior art for this albino C57 ES cell line (C57BL/6J-Tyr$^{c-2J}$ (FIG. 18)) The advantages of using the albino C57 ES cell line in this animal model include: i) fewer mouse colonies will be required because only C57BL/6 will be needed to produce germline transmission and ii) it is easy to choose proper chimeras.

The above described examples 1–4 also describe the present invention in which other albino strains, such as C57BL/10SnJ-TyrC-11J are used. (Results not shown).

Thus, a cost effective, novel and useful approach to developing genetically modified C57 cells and C57 mice as experimental models to facilitate experimental studies of various human diseases is described.

The present invention is not to be limited in scope by the embodiment disclosed in the example which is intended as an illustration of one aspect of the invention and any methods which are functionally equivalent are within the scope of the invention. Indeed, various modifications of the invention in addition to those shown and described herein will become apparent to those skilled in the art from the foregoing description. Such modifications are intended to fall within the scope of the appended claims.

Those skilled in the art will recognize, or be able to ascertain using no more than routine experimentation, any equivalents to the specific embodiments of the invention described herein. Such equivalents are intended to be encompassed by the claims.

What is claimed is:

1. A germline-competent black B6 ES cell line from C57BL/6 mouse strain, wherein said cell line is IC1.

2. A germline-competent white albino B6 ES cell line from C57BL/6J-Tyr$^{c-23}$ mouse strain, wherein said cell line is IAC1.

3. A method of generating a transgenic chimeric mouse, wherein said method comprises:
    introducing a transgene construct into a cell of the IC1 cell line, wherein the transgene construct is stably integrated in the genome of said cell,
    injecting said cell comprising the transgene construct into a C57BL/6 blastocyst, wherein said blastocyst is transplanted into a pseudopregnant mouse, and
    allowing said blastocyst to develop into a chimeric transgenic mouse.

4. A method of generating a transgenic chimeric mouse, wherein said method comprises:
    introducing a transgene construct into a cell of the IAC1 cell line, wherein the transgene construct is stably integrated in the genome of said cell,
    injecting said cell comprising the transgene construct into a C57BL/6 blastocyst, wherein said blastocyst is transplanted into a pseudopregnant mouse, and
    allowing said blastocyst to develop into a chimeric transgenic mouse.

5. The method of claim 3 wherein the chimeric transgenic mouse is identified by PCR and Southern Blot.

* * * * *